(12) United States Patent
Wienecke

(10) Patent No.: US 6,941,009 B2
(45) Date of Patent: Sep. 6, 2005

(54) METHOD FOR EVALUATING PATTERN DEFECTS ON A WATER SURFACE

(75) Inventor: Joachim Wienecke, Jena (DE)

(73) Assignee: Leica Microsystems Jena GmbH, Jena (DE)

( * ) Notice: Subject to any disclaimer, the term of this patent is extended or adjusted under 35 U.S.C. 154(b) by 587 days.

(21) Appl. No.: 09/797,909

(22) Filed: Mar. 5, 2001

(65) Prior Publication Data

US 2001/0036306 A1 Nov. 1, 2001

(30) Foreign Application Priority Data

Mar. 8, 2000 (DE) .......................................... 100 11 200

(51) Int. Cl.$^7$ ................................................. G08K 9/00
(52) U.S. Cl. ....................... 382/149; 382/145; 382/218; 382/305; 356/237.1; 356/394; 250/559.04; 348/126; 348/129
(58) Field of Search ................................. 382/173, 218, 382/305, 149, 145, 159, 318, 304; 250/559.04, 559.42, 559.48, 559.45; 340/130, 129; 356/237.5, 237.1, 338, 445, 394; 348/126, 129; 700/121; 702/35

(56) References Cited

U.S. PATENT DOCUMENTS

| | | | |
|---|---|---|---|
| 4,731,855 A | * | 3/1988 | Suda et al. .................. 382/149 |
| 5,173,719 A | | 12/1992 | Taniguchi et al. ........... 356/394 |
| 5,544,256 A | | 8/1996 | Brecher et al. ............. 382/149 |
| 5,659,630 A | | 8/1997 | Forslund ...................... 382/149 |
| 5,699,447 A | | 12/1997 | Alumot et al. ............... 382/145 |
| 5,801,965 A | | 9/1998 | Takagi et al. ................ 364/552 |
| 5,808,735 A | | 9/1998 | Lee et al. .................... 356/237 |
| 5,825,482 A | | 10/1998 | Nikoonahad et al. ........ 356/237 |
| 5,917,588 A | * | 6/1999 | Addiego .................... 356/237.2 |
| 6,002,791 A | * | 12/1999 | Okada ......................... 382/144 |
| 6,087,673 A | * | 7/2000 | Shishido et al. ........ 250/559.45 |
| 6,178,257 B1 | * | 1/2001 | Alumot et al. .............. 382/145 |
| 6,411,377 B1 | * | 6/2002 | Noguchi et al. .......... 356/237.4 |
| 6,438,438 B1 | * | 8/2002 | Takagi et al. ................ 700/121 |
| 6,757,621 B2 | * | 6/2004 | Mizuno et al. ................ 702/35 |

* cited by examiner

Primary Examiner—Bhavesh M. Mehta
Assistant Examiner—Sheela Chawan
(74) Attorney, Agent, or Firm—Foley & Lardner LLP

(57) ABSTRACT

The invention concerns a method for evaluating pattern defects on a wafer surface, comprising the following steps: acquiring the surface data of a plurality of individual image fields (4) of a series-produced wafer (1); storing the data in a reference data set and making it available as reference data for the inspection of further wafers of the same series; inspecting, successively in time, the individual image fields (4) on the surface of a wafer (1) presently being examined; retrieving from the reference data set a reference datum corresponding to the respective individual image field (4) presently being inspected; comparing the surface of each individual image field (4) currently being inspected to the corresponding reference datum; if one or more deviations are identified, subsequently classifying the deviations into critical and noncritical defects in terms of the functionality of the chip; and simultaneously updating or adding to the reference data set.

18 Claims, 7 Drawing Sheets

METHOD FOR EVALUATING PATTERN DEFECTS ON A WATER SURFACE

CROSS REFERENCE TO RELATED APPLICATIONS

This invention claims priority of a German patent application DE 100 11 200.5 which is incorporated by reference herein.

FIELD OF THE INVENTION

The invention refers to a method for evaluating pattern defects on a wafer surface.

BACKGROUND OF THE INVENTION

Patterned wafers provided for chip production cannot, in practice, be produced without deviations from the ideal pattern. The surface extent of deviations that can negatively affect the functionality of a chip is in the micrometer range. Pattern defects of this kind can be detected, for example, under a microscope.

Deviations can, for example, be classified as to whether or not they make a chip unusable. There may be deviations that cause the chip to be unusable because of their position and characteristics even if they occur only individually. On the other hand, even a larger number of deviations may have no effect on the functionality of the chip.

Automatic examination methods which check, field by field, a chip that has been divided into a plurality of individual image fields, are used to detect the deviations. Given the large number of individual image fields that each contain a large quantity of detailed image data, the high information density means that the amount of data generated cannot be processed quickly enough by computer. Instead, online inspection methods confine themselves initially to the question of whether or not any deviation at all is evident in an individual image field. The comparison is made not to a reference image, but by comparison with a chip or wafer examined immediately previously. The reason this is practical is that the number of random deviations is very small in relation to the number of image points to be examined. Systematic deviations cannot, however, be detected in this fashion.

If the decision as to whether to discard a wafer is to be made not solely as a function of statistically predetermined limit values, it is then necessary to examine those individual images affected by a deviation once again "offline," in a further operation, by removing the wafer in question from the production line. For that purpose, the individual image fields affected by deviations must once again be looked at, in very time-consuming fashion, and individually evaluated by a person; although that person can in some cases utilize preformulated decision rules, he or she must nevertheless often rely on personal examination experience, and in some cases also decide intuitively.

Many of the deviations examined will turn out to be noncritical pseudo-defects, while the risk remains that a critical deviation will be regarded as a harmless pseudo-defect. The relevance of the conclusions reached in this manner, in terms of the decision as to whether a wafer can be released for further processing or must be discarded, is therefore unsatisfactory.

As the technical development of computer chips has proceeded, there has been a continuing miniaturization of surface patterns which is beginning to move away from the microscopically observable realm, so that consequently even smaller deviations become relevant in terms of disruption, and the inspection methods utilized previously are no longer sufficient.

The greater resolution of the individual image fields that is thus also necessary moreover results in a further increase in the image data required for an assessment. There is moreover a tendency toward the use of chips with a greater overall surface area. This, too, is associated with an additional increase in image data, and is incompatible with extensive defect evaluation in the context of automatic defect monitoring in a wafer production line.

In addition, production-engineering aspects must also be considered in the context of wafer defect monitoring methods. For example, a production line for manufacturing wafers should, if possible, never shut down. If, in the context of a continuous examination, each pseudo-defect were to trigger a discard operation for the wafer in question, then a continuous production process would be unimaginable, since practically every wafer exhibits such pseudo-defects.

If an attempt were made with previously known means to perform "online" automated defect evaluation on the basis of the acquired image data for each individual image field that went beyond a yes/no decision in terms of the presence of a deviation, the outlay in terms of computing technology would be immense and would far exceed present-day capabilities.

U.S. Pat. No. 5,825,482, for example, describes a surface inspection system in which a comparison is made with reference data, in which context defects on patterned wafers can be found. The result of the inspection is to provide "wafer plots" which must be interpreted by the operator in terms of process deviations. Automatic evaluation or even classification of identified defects is neither possible nor even provided for.

U.S. Pat. No. 5,173,719 discloses a system which takes into account the fact that circuits have areas with repetitive patterns, and with which both the usual chip comparison and an inspection of the repetitive patterns can be performed simultaneously. For the chip comparison, some of the data are read into a delay-line memory and then compared to the adjacent chip. The inspection of repetitive patterns is accomplished similarly, but the volume of data to be taken into account is much smaller. Two inspection channels operate simultaneously, window control being used for differentiation. Here again, no classification of defects is performed.

U.S. Pat. No. 5,544,256 describes in detail a system that is configured for post-classification of defect locations that have already been found. The basis used is a label image that is calculated from a defect-free reference image. This requires disproportionately high computing performance, with the result that classification proceeds extraordinarily slowly and this system is not suitable for a rapid production sequence.

The aforementioned method is embodied further in U.S. Pat. No. 5,808,735. Here, in order to reduce the false-alarm rate in the classification of defects, a three-dimensional image-to-image comparison is performed. The reference image is described by an array of image points, each image point having defined X-Y-Z coordinates and a defined intensity. The image points of a specific image plane are grouped, and a threshold value is defined therewith. A rapid classification pace can nevertheless be achieved only by limiting the inspection to selected portions of the wafer, so that here again the preconditions for use in a process line are only insufficiently present.

U.S. Pat. No. 5,699,447 presents a two-phase optical method for rapid inspection of all critical layers at a low pseudo-defect rate. In a first phase, the wafer is quickly scanned with a laser, while in the second phase, the locations identified in the first phase as possibly defect-affected are looked at, along with a reference pattern. Images are then generated in various focal planes in order to confirm or rule out the existence of a defect. This procedure is also relatively time-consuming.

To decrease the time expenditure, U.S. Pat. No. 5,659,630 proposes an inspection system in which a binary reference image is generated from the CAD pattern data. The continuous original image of the pattern being examined is binarized, and the two images are then subjected to a specific comparison for each defect type. The disadvantages are on the one hand the fact that signal processing is still too slow, and on the other hand the hardware and software outlay necessary for each individual defect type. This system also possesses only limited variability, since the hardware for new defect types cannot readily be programmed.

U.S. Pat. No. 5,801,965 presents a system and a method in which defect detection and defect classification are integrated into a process control system. The system uses two measuring instruments, however, and thus also possesses the disadvantages already cited.

SUMMARY OF THE INVENTION

Proceeding therefrom, it is the object of the invention to create a method for defect evaluation on patterned wafers that allows, with high reliability, a distinction between defects impairing the functionality of a chip (critical defects) and defects that do not impair functionality (noncritical defects).

This object is achieved by way of a method for evaluating pattern defects on a wafer surface, in which surface data of an individual image field of the wafer surface that have just been acquired are compared to electronically stored reference data that have been generated from previously acquired surface data of identically located individual image fields from a plurality of wafer surfaces of the same production series and pattern.

In detail, the method comprises the following steps: acquiring the surface data of a plurality of differently located individual image fields of the wafer surface; comparing the surface data of each individual image field to a reference datum from a reference data set in which all the previously acquired surface data of the identically located individual image fields of wafers having the same pattern are stored; ascertaining deviations as a result of the comparison; classifying into critical and noncritical deviations; and outputting advisories as to the individual image fields of the wafer surface having critical deviations.

Advantageously, provision is made for the comparison of the surface data of a first individual image field to the reference data set, the ascertaining of deviations, and the classification thereof, to be accomplished in temporally parallel fashion with the acquisition of the surface data of a second individual image field. Then the comparison of the surface data of the second individual image field to the reference data set, the ascertaining of deviations, and the classification thereof are performed in temporally parallel fashion with the acquisition of the surface data of a third individual image field, and so forth.

The approach according to the present invention allows a wafer inspection process that can be performed online in a production line. In contrast to conventional methods, not only is a yes/no check in terms of the presence of deviations in the individual image fields accomplished, but also a differentiation of the defects. What is exploited for this purpose is the fact that deviations do not occur in each individual image field, so that the time during which a deviation-free individual image field of this kind is being acquired and compared to a reference data set can be used to analyze the deviations in an individual image field that was acquired earlier.

Because of this parallelization of the acquisition of the individual image fields and the more thorough examination of those individual image fields in which deviations were identified, in combination with the use of the data from wafers examined earlier, it is possible to determine the deviations relevant to the functionality of a chip efficiently and with high reliability. The number of false alarms, which are based on an incorrect evaluation of a pseudo-error as a critical error, can be drastically decreased.

The error assessment possible with the method according to the present invention is moreover independent of whether or not individual patterns repeat on the wafer or within a chip or even within an individual image field, or whether they possess regular or stochastic properties. In addition, it is now possible to identify systematic errors that heretofore could not be detected.

Since the method according to the present invention dispenses with offline post-inspection, the result is a considerable simplification in operation and an appreciable time savings in wafer inspection, together with improved relevance of the conclusions as to whether the wafer can continue to be used.

In an advantageous embodiment of the invention, in order to generate the reference data sets, surface data for the individual image fields are acquired on the basis of a larger number of wafers, and analyzed according to various parameters. The reference data sets for the information base are permanently stored. Based on this information base, it is then possible to make a rapid analysis of the wafer being examined during an online checking method.

This procedure furthermore has the advantage that the information base can be ascertained with the same device that is later also used to inspect the wafers. When the wafers being produced are switched over to a new pattern, this device can thus easily be adapted to a new wafer pattern in a learning procedure.

In contrast to the use of the design data for the wafer or the individual chip as the only information base, with the procedure according to the present invention it is possible to eliminate misinterpretations that result from the device used for the examination. It is certainly advantageous, however, to expand the information base to include the design data, since the latter data provide, for example, information regarding the segmentation of the wafer and of the individual chips which can be utilized to estimate the effect of a deviation. In the context of efficient data management, it may also be advantageous if patterns which repeat on a wafer are stored together in the information base and only once for all relevant individual image fields.

To eliminate any interruptions in online inspection of the wafers it is advantageous if, when a deviation is identified, the surface data of the individual image field in question are stored in an intermediate buffer, from which they are then conveyed to an analysis apparatus for more thorough examination. Since more thorough examination of the individual image fields generally requires more time than checking an individual image field for the presence of a deviation, intermediate buffering eliminates the need for a process interruption in line production when defects occur in individual image fields inspected immediately after one another.

The individual image field containing a deviation is retained in the intermediate buffer until the individual image fields previously stored therein have been checked in the analysis apparatus.

In a further embodiment, the associated reference data sets of the information base are also simultaneously stored in the intermediate buffer, and from there are conveyed to the analysis apparatus together with the surface data of the individual image field. The more thorough examination of individual image fields which have deviations is thus independent of the inspection of further individual image fields. More thorough examination of an individual image field thus does not interfere with continuation of the inspection of further individual image fields on the wafer, which thus can be performed without interruption.

In a further advantageous embodiment of the invention, the deviations are classified into different defect types, and displayed visually with the allocation as to the respective defect type. Because the defects are classified according to criteria which are optionally defined by the user, the greater transparency resulting therefrom makes it possible to draw conclusions as to the causes of the defects, so that suitable countermeasures can be taken more quickly.

Preferably, several reference data sets together allow a segmentation of individual image fields into regions each having similar surface patterns. Classification of the defect types is performed, in this context, according to the location of the deviations in the various pattern regions. This segmentation, and the allocation of the individual deviations to the various pattern regions, makes it possible to achieve high-quality categorization of the deviations into critical and noncritical defects. The reason for this is that the individual deviations are no longer considered merely with reference to their position, but rather are assessed in the context of their environment. Incorporating this environmental data into the defect classification makes it possible to maximize detection sensitivity.

The segmentation of the individual image fields can be derived, for example, from the design data for the wafer. It is also possible, however, to use the segmentation when generating the reference data sets of the information base, suitable image analysis algorithms being utilized.

In a further advantageous embodiment of the invention, definition of the defect types is performed on the basis of a combination of analysis parameters of the surface data of known defects. In this context, the subdivision of defect types into different classes is greatly dependent on the type of wafer or chip being examined, and must consequently be suitably adapted to it. Definition of the defect types must be accomplished before the actual inspection of the wafers being examined, for example upon generation of the information base; this does not, however, rule out (in the event new defects occur later) the corresponding definition of new defect types and their use for classification. Indeed, a process of instructing the analysis apparatus that continues even during inspection makes it possible to improve further the detection accuracy for defects, and the exclusion of pseudo-defects. This information can be stored in the reference data sets.

For inspection or also for analysis of the individual image fields, it is possible to use a variety of analysis methods with which, inter alia, different kinds of data regarding the surface within an individual image field can be obtained. Corresponding to these different kinds of surface data are respectively allocated different types of reference data sets in the information base, with which, upon more-thorough examination of an individual image field containing a deviation, conclusions as to the characteristics of the deviation can be drawn. Analysis of the individual comparisons is, however, comparatively time-consuming and not practical during an online inspection method. The question as to whether an individual image field should be examined more closely therefore requires a reduction in the volume of data necessary for an initial comparison. This is preferably achieved by the fact that the same type of reference data set is used for the initial examination of all the individual data fields, the preferred type being one which permits a highly reliable conclusion for all possible surface patterns occurring in the individual images.

In an alternative embodiment, the relevance of the conclusions can be improved by selecting a specific type of reference data set as a function of the individual image field to be examined, the individual image fields being categorized into classes and one type of reference data set being allocated to each individual image field class. The basis for the selection thereof must be that the volume of data necessary for an initial comparison not result in a disproportionately long analysis time, but on the other hand possess sufficient relevance in terms of the resulting conclusion. Since the allocation to classes of the individual image fields remains unchanged when similar wafers are being examined, it is advantageous if this information regarding the respective individual image fields is stored in location-dependent fashion in the information base. Upon inspection of an individual image field, the relevant reference data set is then automatically selected for identification of a deviation, on the basis of the class that is stored in the information base and allocated to the relevant individual image field.

Alternatively, it is also possible, upon inspection of the individual image field, to ascertain the relevant class from the examination data that are immediately available, and with them to select the reference data set that is relevant for the initial examination.

Preferably, in order to improve analytical accuracy, a predetermined method for inspecting the wafer and/or specific inspection parameters are established as a function of the class of the individual image field being acquired. The resolution and the focus state of a focusable inspection apparatus, inter alia, are suitable for this purpose.

The deviations occurring on the surface of the wafer are often not exclusively point-like in nature or entirely independent of one another. For example, deviation clusters which extend beyond the boundaries of the individual image fields or the individual chips can occur. If a defect analysis is confined only on the individual deviations, then, for example, mask defects or macroscopic objects are not recognized in terms of their correlation. In an advantageous embodiment of the invention, after classification of the deviations in terms of defect type, an examination of the defect-affected individual fields is therefore performed to determine whether they are directly adjacent to one another. This information makes it possible, above all, better to assess those defects that happen to lie on a boundary between two individual image fields.

By way of an examination of the defects, by defect type, in terms of their position with respect to one another on the wafers, it is possible to identify the aforementioned mask defects on a chip, or scratches on a wafer.

BRIEF DESCRIPTION OF THE DRAWINGS

The invention will be explained in more detail below with reference to drawings, in which.

DETAILED DESCRIPTION OF THE INVENTION

The invention is based on the following initial considerations:

Firstly, it is assumed that the pattern on a wafer is known from the design of the chips arranged on the wafer. This means that comparative information is already available even before any inspection of the wafer surface begins. In addition, the importance of the individual patterns on the chips in terms of the latter's functionality is known. It is consequently ineffective to consider the environment of the deviation only when a deviation is detected, in order to be able to draw conclusions therefrom for the characterization or classification of defects.

It is also assumed that as a rule, a very large number of wafers with a correspondingly great number of similar chips is being manufactured. It is consequently worthwhile to spend more time creating a comparison base that can be used efficiently to ascertain deviations or defects.

The most successful method for defect determination is a comparison among similar objects. This method moreover makes it easy to change to a new pattern. The differentiation of defects and pseudo-defects, and optionally the differentiation of defects into individual defect types, requires both the defect image and a comparison image, the term "image" being understood here as image data. While preparation of the defect image does not entail any great effort, preparation of the comparison image entails greater difficulties.

In the inspection of wafers, all of the information concerning the wafer and the chips present on it is broken down into information about a plurality of individual image fields. The number of individual image fields for complete inspection of one wafer is very large (on the order of several hundred thousand). The number of deviations that must be looked at in greater detail is on the order of approximately 1,000. This means, however, that the time required for classification of a deviation can be longer than the inspection time for an individual image field, by an amount equal to the ratio between the number of individual image fields and the number of individual image fields to be classified.

Figure 1:
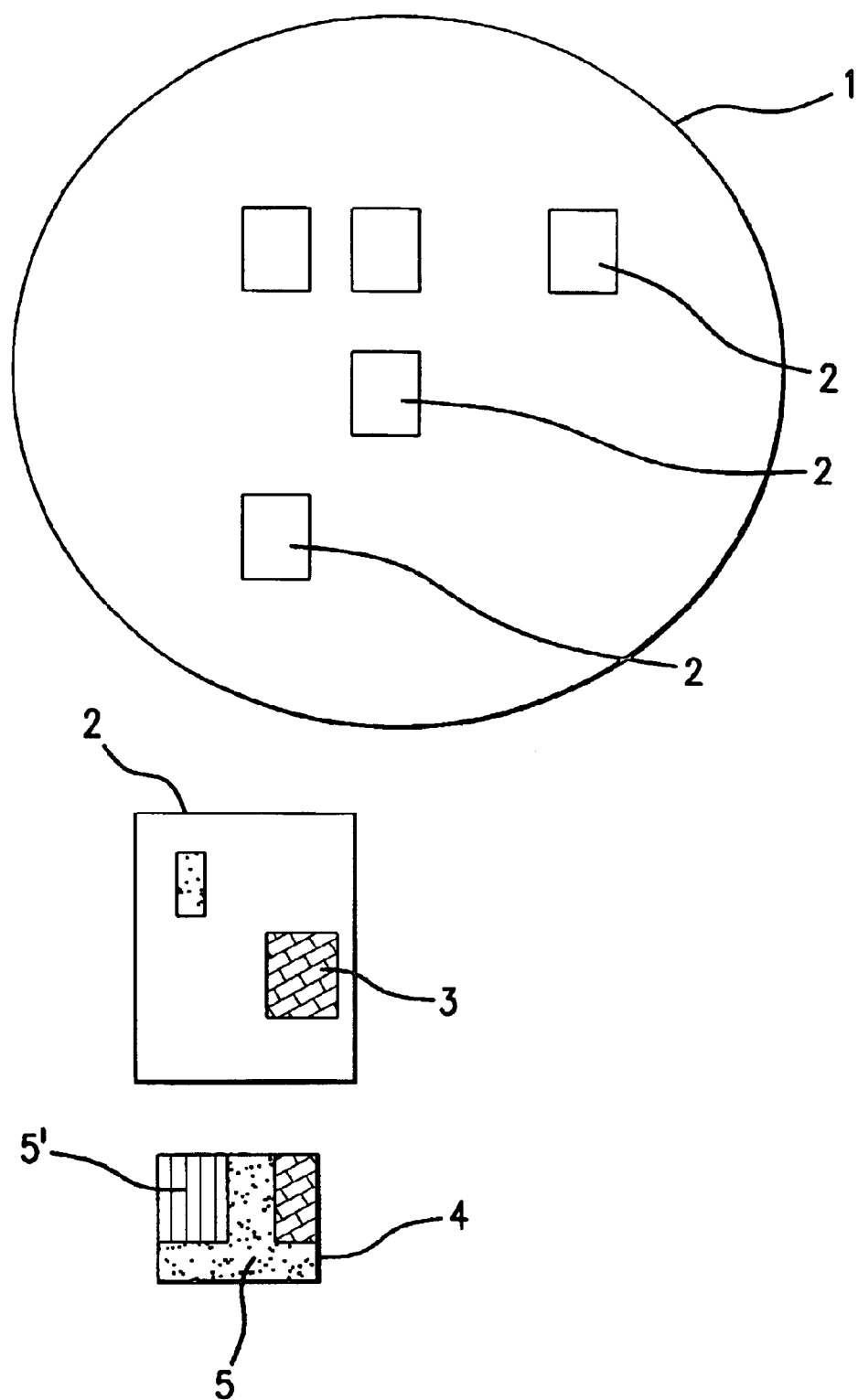
FIG. 1 is a depiction to illustrate wafer segmentation, chip segmentation, and individual image field segmentation.

The volume of surface data present on a wafer and requiring analysis is so great that it must be segmented. One procedure for doing so is depicted by way of example in FIG. 1, from top to bottom.

Segmentation of wafer 1 involves first the information as to how many chips 2 are present on it, and the locations at which chips 2 are arranged with reference to an absolute coordinate system.

On a lower hierarchical level, chip 2 is then segmented into typical regions 3; on the basis of this subdivision, it is then possible to define or ascertain which regions 3 are inspected and classified with a particular inspection method and/or inspection parameter, for example the resolution or focusing of an inspection device.

Since the surface data of a chip 2 cannot itself be acquired all at once, it must be divided into a plurality of individual image fields 4. Each of these individual image fields 4 is in turn split up into areas 5, 5' having similar surface patterns. By way of this individual image field segmentation, deviations that occur can be assessed in the context of their environment; as stated above, the importance of the individual areas 5, 5' on chip 2 is already known from the design phase of the chip.

Based on this information, for example, a distinction can be made as to whether a defect is located in a region that is critical or noncritical in terms of the function of chip 2, or also, for example, as to whether the deviation is located in a function-critical segment but is not of function-critical size. This information is stored in the reference data sets. This kind of data linkage makes it possible to achieve a high level of accuracy in the detection of defects and pseudo-defects.

Two methods for defect evaluation on patterned wafers will now be explained in more detail with reference to FIG. 2 and FIG. 3, both procedures being based on the method principles according to the present invention.

Before any online inspection of wafers can be performed, it is first necessary to create an information base with reference data sets for the individual image fields of the wafer that will later be examined. This database covers, as it were in the manner of a multi-layer "map," all the relevant areas of a wafer, which are not necessarily limited to the chip portions. The individual layers of the "map" contain data, sorted according to various criteria (for example, analysis parameters), about the surface configuration of a fictitious reference wafer. Each layer can be combined, for one individual image field, into a reference data set and stored in a central memory.

Before an inspection operation, criteria for differentiating deviations into defects and pseudo-defects must also be prepared and made available for the inspection process.

Only after this can the online inspection be made of the wafer that is to be examined. In this context, the individual image fields of interest are individually introduced, in succession, into an optical measurement device and optically examined by acquiring data about the surface of the respective individual image field. In a first examination step, these data are compared to a suitable reference data set, for example by way of a pixel-based image-to-image comparison, to ascertain any deviations.

If at least one deviation is identified, a closer examination of the acquired surface data is conducted in a further examination operation, in which several or all reference data sets for the relevant individual image field are compared to the surface data acquired for the latter. This operation is, however, advantageously separated out from the inspection and initial examination of the individual image fields which takes place in a timed cycle, and is executed only as necessary (i.e. only when a deviation is identified), in temporally parallel fashion with the time-cycled examination of the individual image fields.

Figure 2:
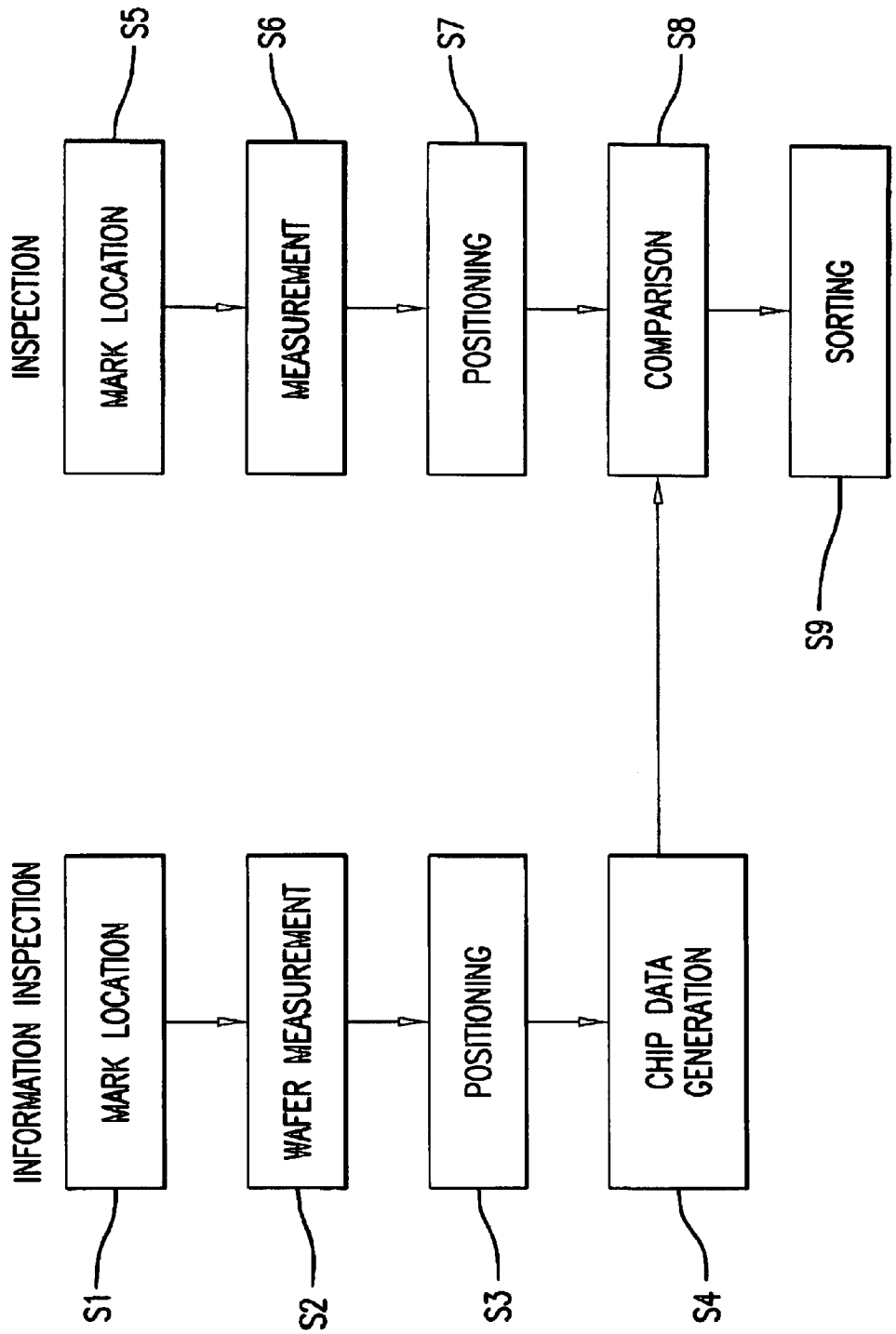
FIG. 2 schematically depicts the method steps for defect assessment on a patterned wafer, in which a differentiation can be made into critical defects and noncritical defects (pseudo-defects)
Figure 3:
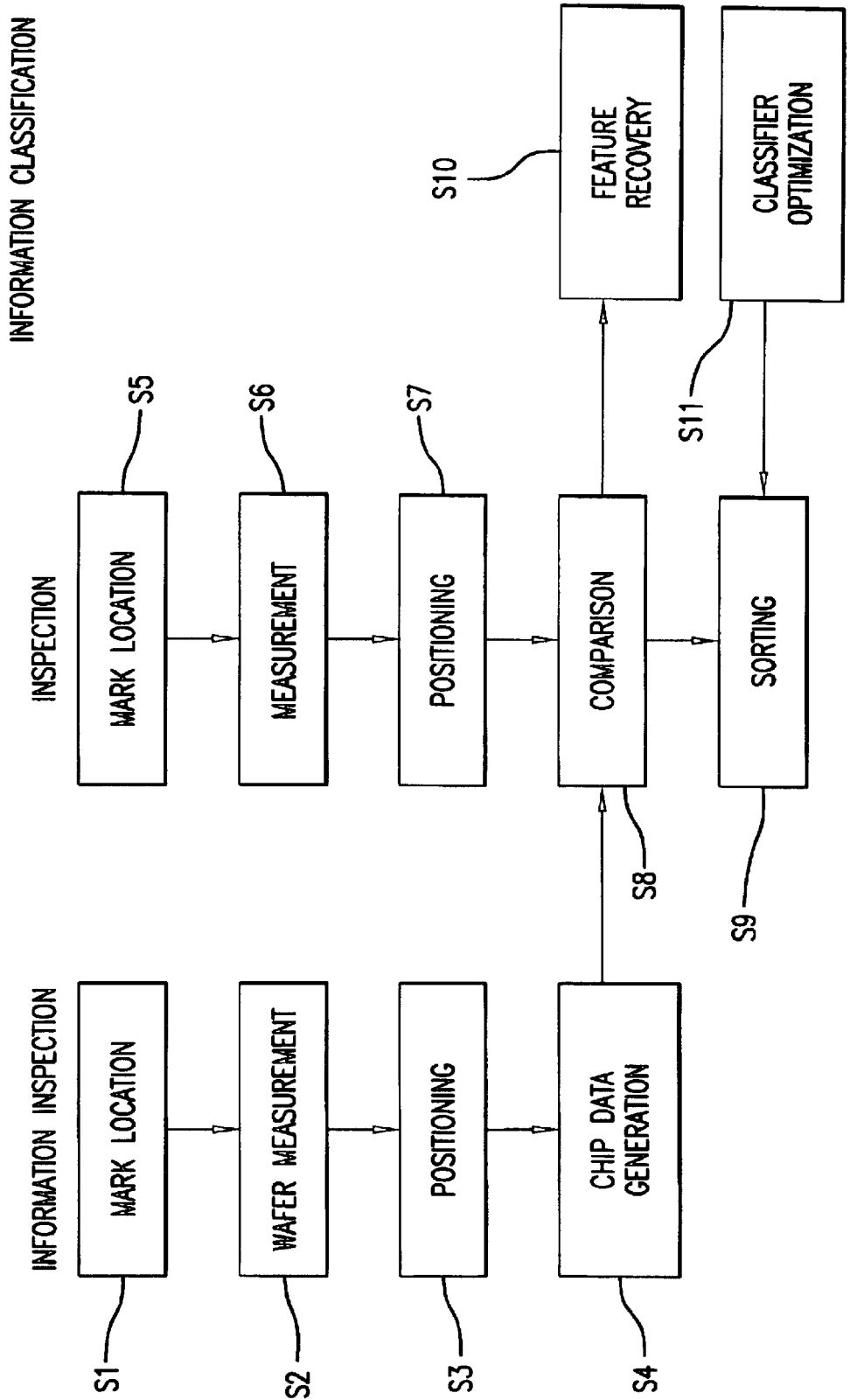
FIG. 3 shows a further method for defect assessment in which the defects that occur are classified into various types.

FIGS. 2 and 3 each show, on the left side, the instruction of an apparatus for defect analysis. Mark location S1, wafer measurement S2, and positioning S3 ensure that the images of identical chips are acquired with sub-pixel accuracy among one another during scanning of the individual image fields. In order to generate the reference data sets for the information base (step S4), which in a manner of speaking represents a fictitious reference wafer, several wafers or chips are analyzed one individual image field at a time. For the sake of high accuracy, this operation proceeds at a slower speed than the later inspection of the wafers that are to be examined.

From the data for the individual wafers or chips, valid comparison data are generated for the reference wafer or for a reference chip. These comparison data are stored, for example, in the form of data in a chip memory. Averaged images, the mean square deviations of parameters acquired in location-dependent fashion, multi-label images combined with material properties, or CAD or mask data, are principally suitable for this purpose.

Figure 4:
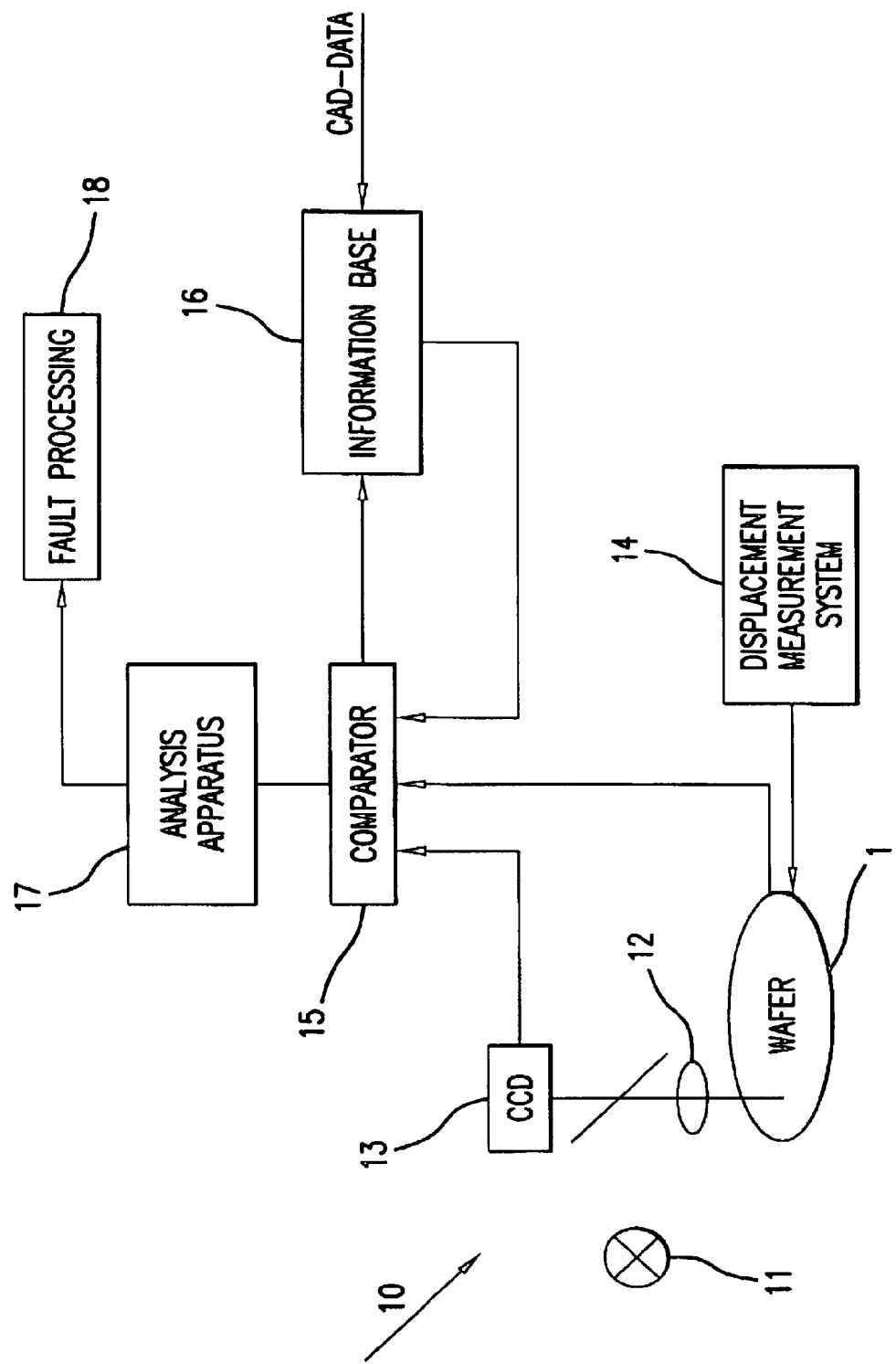
FIG. 4 schematically depicts an arrangement for carrying out the method of FIG. 2.
Figure 5:
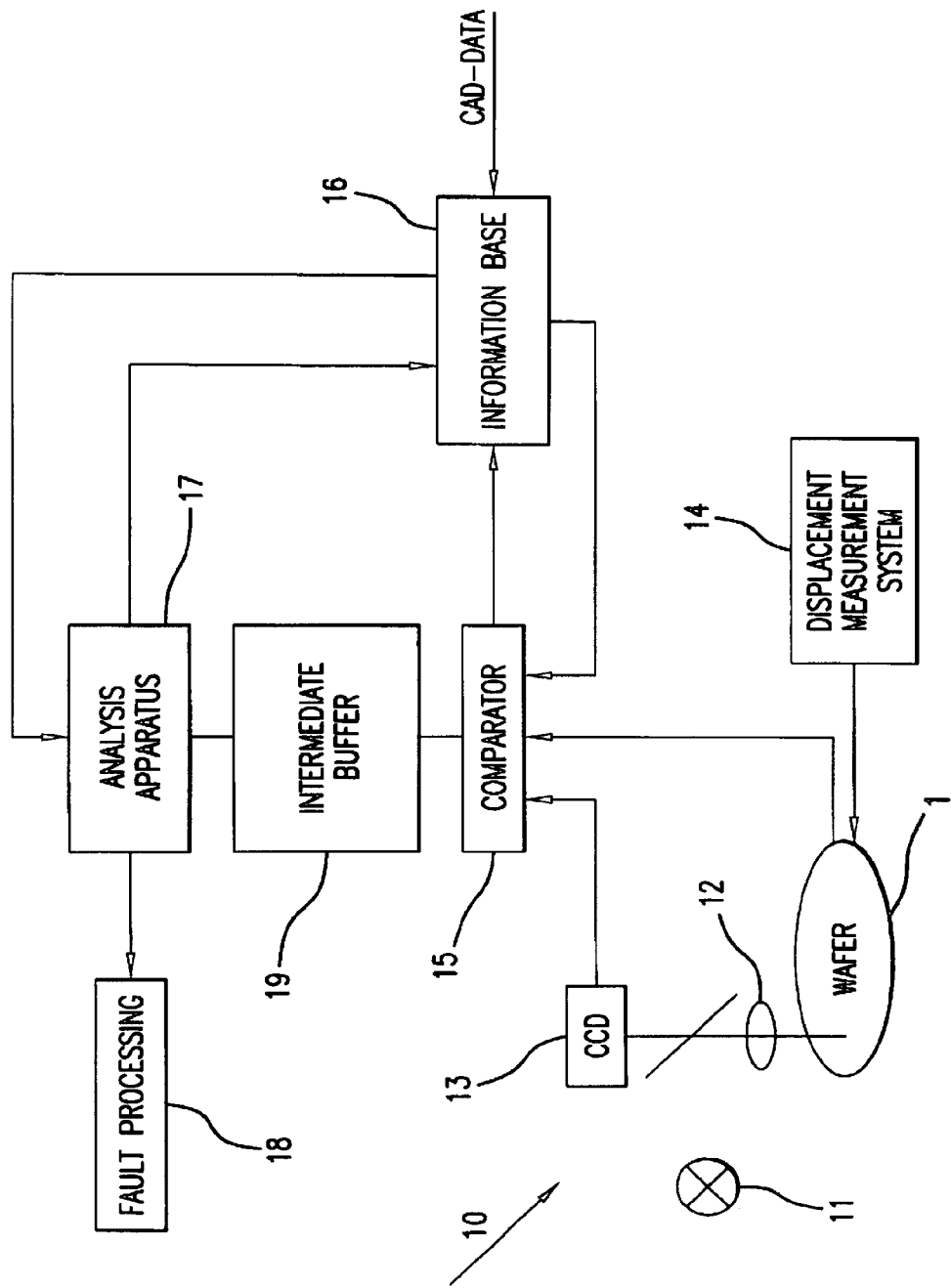
FIG. 5 schematically depicts an arrangement for carrying out the method of FIG. 3.

The actual inspection operation is accomplished using an optical measurement device 10 indicated in FIG. 4 and FIG. 5. In this context, by way of a laser-controlled stage which carries wafer 1, individual image field 4 that is to be inspected is positioned with respect to optical measurement device 10—which for example comprises an illumination source 11, an objective 12, and a CCD detector 13—and scanned.

For a successful inspection, it is necessary to guarantee the most accurate possible association (preferably to sub-pixel accuracy) between individual image fields 4 and the absolute coordinate system of wafer 1. For that purpose, individual image fields 4 are successively brought in on a timed cycle by the laser-controlled stage, which is coupled to an automatic displacement measurement system 14, and optically scanned. In order to reduce movement blur and allow an increase in effective exposure time, the stage operates on a start-stop basis.

As indicated in FIG. 2, after mark location S5, measurement S6, and positioning S7, a comparison S8 of the acquired surface data to a selected reference data set, which was generated in a "chip data generation" step S4 and is stored in information base 16 (cf. FIG. 4), is performed during inspection for each individual image field 4. For that purpose, the surface data of the individual image field 4 that was just acquired, and the coordinates of the displacement measurement system, are conveyed to a comparator 15 (see FIG. 4). Based on the location of the image field thereby determined, comparator 15 retrieves from information base 16 the data relevant to individual image field 4 in question, on the basis of which a decision is made as to whether or not a deviation exists in individual image field 4 that has just been acquired. The result is sorting step S9.

Comparator 15 can use the same type of reference data set for each individual image field. Since individual image fields 4 that are being examined can vary greatly in terms of their pattern depending on the region of chip 2, there also exists the possibility of using for the analysis, based on information known per se and stored in information base 16, a reference data set that possesses a particularly high significance for the particular surface patterns in terms of identifying a deviation.

If such a deviation is identified, the acquired surface data of the relevant individual field 4, as well as the reference data sets of the information base present in that context, are passed on to an analysis apparatus 17 in which, according to suitable criteria and in parallel with the continuing examination of subsequent individual image fields 4, a more thorough examination is made on the basis of predefined classification criteria, allowing classification of a deviation as either a defect or a pseudo-defect (cf. sorting step S9 in FIG. 2).

Figure 6:
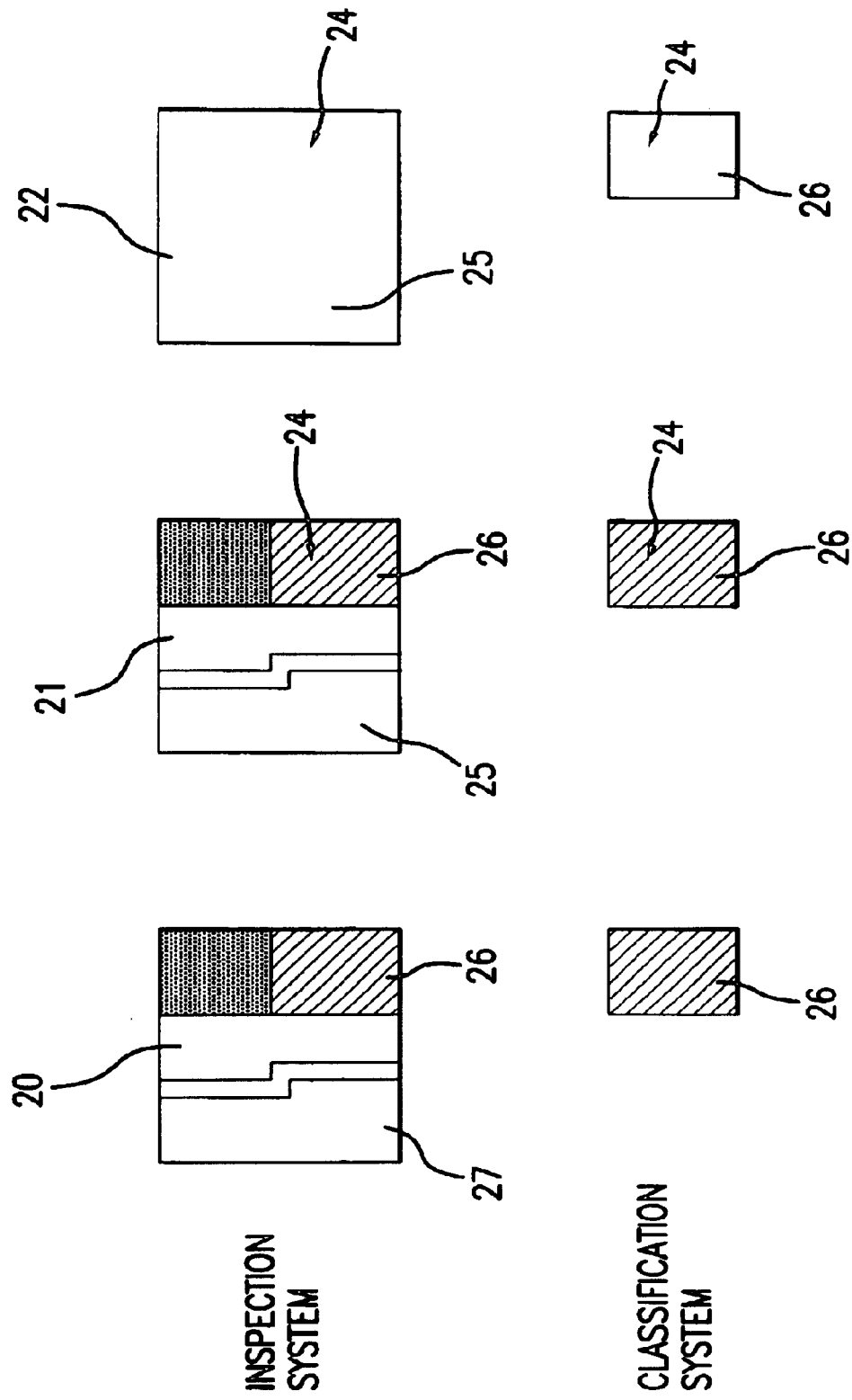
FIG. 6 shows a segmented individual image field with an ideal pattern depicted at the left, a real pattern depicted at the center, and a defect image depicted at the right, to illustrate a first manner of defect classification.

For this purpose, analysis apparatus 17 is instructed prior to the inspection on the basis of known defects; the defects can be characterized with reference to image field segments with different surface patterns, or a combination of analysis parameters of surface data, or based on a combination of such data, as depicted for example in FIG. 6. Shown in the latter at left is reference individual image field 20, stored in information base 16, from which real individual image field 21 differs by having two surface deviations (defects 24 and 25). From an image comparison, defect image 22 (shown at right) is obtained for individual image field 4 in question; in the present case, that would be a reason to examine the acquired real individual image field 21 on the basis of further data stored in information base 16 via the associated reference individual image field 20.

In the present example, what occurs in this further examination is an allocation of defect 24 to a specific segment 26 of reference individual image field 20, which in this case is to be considered a region essential to the functionality of the chip. In contrast, the light-colored left-hand segment 27 of reference individual image field 20, which also has a deviation (defect 25) in real individual image field 21, constitutes a region not relevant to the functionality of chip 2 and need not be examined more closely. This categorization of the deviations in the context of their environment thus allows the deviations to be classified as critical defects 24 which impair the functionality of the chip, and noncritical defects (25), or so-called pseudo-defects, which do not impair the functionality of the chip.

Figure 7:
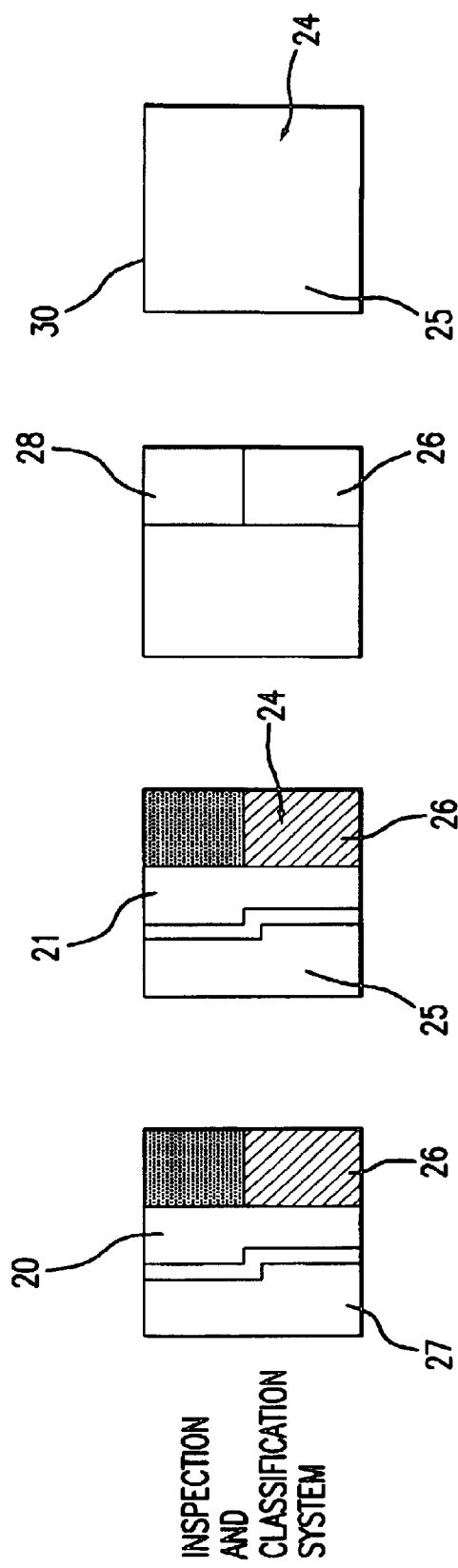
FIG. 7 shows a further procedure for defect classification.

A further exemplary embodiment is depicted in FIG. 3, FIG. 5, and FIG. 7. The principal difference between this exemplary embodiment and the exemplary embodiment explained previously is the further examination of critical defects 24, which are to be differentiated into different defect types in order to provide users with further interpretation possibilities for the determination of causes. As is evident from FIG. 5, the corresponding apparatus has an intermediate buffer 19, downstream from comparator 15, to which the acquired surface data (and optionally also the allocated reference data sets) are transferred in the event a deviation is identified in an individual image field 4. Intermediate buffer 19 acts as the input side of an analysis apparatus 17, and prevents any interruption in the inspection operation from taking place if deviations occur in adjacent or immediately successive individual image fields 4.

As in the previous exemplary embodiment, a distinction is made in analysis apparatus 17 between defects and pseudo-defects, although the defects are sorted into type classes. For example, the defects, and if necessary the pseudo-defects as well, can be output in a list; in the context of the second exemplary embodiment, the defects can be presented in order by type class. It is also possible to visualize the identified defects over the wafer surface, or to select a different form of depiction.

In FIG. 7, in addition to a pattern description 28 of the relevant real individual image field 21, a corresponding defect image 30 is output, both critical defects 24 and the pseudo-defects or noncritical defects 25 being depicted. By way of suitable filters, however, a presentation separated according to pseudo-defects and critical defects can also be made, and can moreover be limited to individual type classes.

To reduce the volume of information to be received by intermediate buffer 19, it is also possible to store in intermediate buffer 19 only individual image field 4 that was just acquired and exhibits a deviation, or its surface data. The reference data sets additionally necessary for defect evaluation then need to be loaded into analysis apparatus 17 from information base 16—i.e. in this case from the central memory—at the time the respective individual image fields are processed.

Definition of the defect types is accomplished in a multi-stage process (feature recovery step S10 and classifier optimization step S11, in FIG. 3). For this purpose, for example, previously unknown deviations are defined with respect to the reference wafer already stored in the information base. The features of these deviations, i.e. for example specific analysis parameters such as color and brightness information, are determined and are visualized in suitable fashion, the deviation simultaneously being considered in the context of the surrounding surface pattern. The user can then interactively define the manner in which the defect classes are to be subdivided, or the defects to be searched for. Once the analysis apparatus has been correspondingly instructed, all further wafers can be evaluated with the same set of questions.

FIG. 3 also shows that even after an initial instruction of analysis apparatus 17, the defect type classification can be adapted or expanded as necessary based on the recognition of further defects during the inspection of wafers 1.

The evaluated defects are, for example, stored in a list that once again can be organized with reference to the basic unit of wafer 1. The defect type classification depicted in general fashion in FIG. 6, in terms of the individual segments 26 of individual image field 4, makes it possible to detect, with high reliability, defects that are critical to the functionality of a chip 2. In addition, the decoupling of image segmentation from defect detection and defect classification by way of the information base for pattern classification means that more complex and more powerful algorithms can be utilized, since the information necessary for inspection and classification has already been prepared in an instruction phase.

Figure 8:
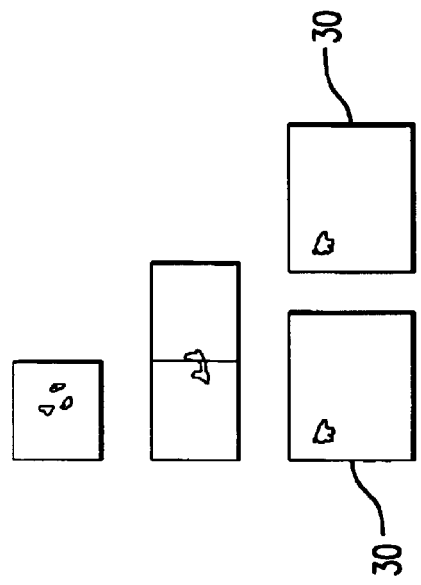
FIG. 8 shows an illustration of the clustering of defects.

The latter purpose is also served by a clustering process. As depicted by way of example in FIG. 8, after defect detection and classification, the information is combined (as shown from bottom to top). The goal here is to prevent defects from being split up during subdivision into image fields, to ensure correct defect allocation, and also to prevent double-counting of defects.

PARTS LIST

1 Wafer
2 Chip
3 Region
4 Individual image field
5,5' Areas
10 Measurement device
11 Illumination source
12 Objective
13 CCD detector
14 Displacement measurement system
15 Comparator
16 Information base
17 Analysis apparatus
19 Intermediate buffer
20 Reference individual image field
21 Real individual image field
22 Defect image
24 Critical defect
25 Noncritical defect
26,27 Segments
28 Pattern description
30 Defect image
S1 Mark location
S2 Wafer measurement
S3 Positioning
S4 Chip data generation
S5 Mark location
S6 Measurement
S7 Positioning
S8 Comparison
S9 Sorting
S10 Feature recovery
S11 Classifier optimization

What is claimed is:

1. A method for evaluating pattern defects on a wafer surface comprising the following steps:

acquiring surface data of a plurality of differently located individual image fields of the wafer surface;

comparing the surface data of each individual image field to a reference datum from a reference data set in which all the previously acquired surface data of the identically located individual image fields of other wafers having the same pattern are stored;

ascertaining deviations as a result of the comparison;

classifying the deviations into critical and noncritical defects; and outputting advisories as to the individual image fields of the wafer surface having critical defects.

2. The method as defined in claim 1, wherein electronically stored reference data in the reference data set have been generated from previously acquired surface data of identically located individual image fields from a plurality of wafer surfaces of the same production series and pattern.

3. The method as defined in claim 2, wherein the comparison of the surface data of a first individual image field to the reference data set, the ascertaining of deviations, and the classification thereof are accomplished in temporally parallel fashion with the acquisition of the surface data of a second individual image field; then the comparison of the surface data of the second individual image field to the reference data set, the ascertaining of deviations, and the classification thereof are performed in temporally parallel fashion with the acquisition of the surface data of a third individual image field; and so forth.

4. The method as defined in claim 2, wherein in order to obtain a reference data set, the surface data of identically located individual image fields of a plurality of wafers having the same pattern are acquired, and are analyzed according to various parameters.

5. The method as defined in claim 1, wherein when a deviation is identified, the surface data of the corresponding individual image field are stored in an intermediate buffer, and from there are conveyed to an analysis apparatus in which classification based on defect types is performed.

6. The method as defined in claim 5, wherein the associated reference data sets are also stored in the intermediate buffer, and from there are conveyed to the analysis apparatus along with the buffered surface data of individual image fields.

7. The method as defined in claim 1, wherein the deviations are classified into different defect types, and wherein output are displayed visually with the allocation as to the respective defect type.

8. The method as defined in claim 1, wherein a segmentation of an individual image field into regions each having similar surface patterns is performed; and the classification of the defect types is performed according to location with respect to the various surface pattern regions.

9. The method as defined in claim 1, wherein the definition of the defect types is performed on the basis of a combination of analysis parameters of the surface data of known defects.

10. The method as defined in claim 1, wherein for all individual image fields, the same type of reference data set is selected for a first comparison of the acquired surface data.

11. The method as defined in claim 1, wherein a specific type of reference data set is selected for a first comparison as a function of the individual image field to be examined, the individual image fields being categorized into classes and one type of reference data set being allocated to each individual image field class.

12. The method as defined in claim 11, wherein the information regarding an allocation of an individual image field to a class is stored together with a location datum in an information base; and that upon inspection of an individual image field, the reference data set to be used for the first comparison is selected on the basis of the class that is stored in the information base and allocated to the relevant individual image field.

13. The method as defined in claim 11, wherein upon inspection of an individual image field, firstly its class is ascertained from data of the individual image field, and with them the reference data set is then selected.

14. The method as defined in claim 11, wherein a predetermined method for inspecting the wafer and/or specific inspection parameters are established as a function of the class of the individual image field.

15. The method as defined in claim 14, wherein the inspection parameters comprise the resolution and a focus state of a focusable inspection apparatus.

16. The method as defined in claim 1, wherein after classification of the deviations in terms of defect type, the defect-affected individual image fields are examined as to whether they are directly adjacent to one another.

17. The method as defined in claim 1, wherein after classification of the deviations in terms of defect type, all defects are examined in terms of their position on the wafer.

18. The method as defined in claim 1, wherein the step of acquiring surface data of a plurality of differently located individual image fields is performed without first scanning the whole wafer surface.

* * * * *